(12) United States Patent
Brown et al.

(10) Patent No.: US 11,053,255 B2
(45) Date of Patent: Jul. 6, 2021

(54) SYNTHESIS OF MAHANINE AND RELATED COMPOUNDS

(71) Applicant: Georgetown University, Washington, DC (US)

(72) Inventors: Milton L. Brown, Brookeville, MD (US); Shujie Hou, Gaithersburg, MD (US)

(73) Assignee: GEORGETOWN UNIVERSITY, Washington, DC (US)

(*) Notice: Subject to any disclaimer, the term of this patent is extended or adjusted under 35 U.S.C. 154(b) by 0 days.

(21) Appl. No.: 15/189,512

(22) Filed: Jun. 22, 2016

(65) Prior Publication Data

US 2016/0368927 A1  Dec. 22, 2016

Related U.S. Application Data

(60) Provisional application No. 62/182,706, filed on Jun. 22, 2015.

(51) Int. Cl.
*C07D 491/052* (2006.01)
*C07D 491/048* (2006.01)

(52) U.S. Cl.
CPC .................. *C07D 491/048* (2013.01)

(58) Field of Classification Search
CPC .................................................. C07D 491/052
USPC ......................................................... 548/421
See application file for complete search history.

(56) References Cited

U.S. PATENT DOCUMENTS

| | | | |
|---|---|---|---|
| 3,046,121 | A | 7/1962 | Schmidt |
| 3,965,703 | A | 6/1976 | Barnhardt |
| 5,677,328 | A | 10/1997 | Takaki |
| 6,037,362 | A | 3/2000 | Miyoshi |

FOREIGN PATENT DOCUMENTS

| | | | |
|---|---|---|---|
| CA | 2575046 | 2/2006 | |
| CA | 2719457 | 10/2009 | |
| EP | 0389037 A1 * | 9/1990 | ........... C07D 405/12 |
| EP | 0679641 | 11/1995 | |
| EP | 1184373 | 3/2002 | |
| EP | 1238973 | 9/2002 | |
| EP | 1352650 | 10/2003 | |
| EP | 1918711 | 5/2008 | |
| WO | 9402483 | 2/1994 | |
| WO | 9932463 | 7/1999 | |
| WO | 0183452 | 8/2001 | |
| WO | 00027434 | 11/2001 | |
| WO | 2002006255 | 1/2002 | |
| WO | 2002060867 | 8/2002 | |
| WO | 2002074306 | 9/2002 | |
| WO | 2005016922 | 2/2005 | |
| WO | 2006002908 | 1/2006 | |
| WO | 2007014687 | 2/2007 | |
| WO | 2007036131 | 4/2007 | |
| WO | 2007042912 | 4/2007 | |
| WO | 2009086472 | 7/2007 | |
| WO | 2007026203 | 8/2007 | |
| WO | 2008051523 | 5/2008 | |

OTHER PUBLICATIONS

Hou, S., Y. Liu, Y. Kong, and M. Brown "Total Synthesis of 7-Hydroxymurrayazolinine, Murrayamine D, and Mahanine via m-Nitro group activated Pyran Annulation" Org. Lett. (2015), 17: pp. 2298-2301.*
Hou, S., Y. Liu, Y. Kong, and M. Brown "Total Synthesis of 7-Hydroxymurrayazolinine, Murrayamine D, and Mahanine via m-Nitro group activated Pyran Annulation" Org. Lett. (2015), 17: pp. 2298-2301. (Year: 2015).*
Curtis, N., J. Prodger, G. Rassias and A. Walker, "A facile gold(I)-catalysed intramolecular alkyne hydroarylation approach to methyl 5-amino-2H-1-benzopyran-8-carboxylate derivatives" Tetrahed. Lett. (2008), 49: pp. 6279-6281. (Year: 2008).*
Roeske, R., "Carboxyl Protecting Groups" The Peptides: Analy., Syn., Biol. (1981), vol. 3: pp. 101-139. (Year: 1981).*
Wulff, J., S. Herzon, R. Siegristand A. Myers, "Evidence for the Rapid Conversion of Stephacidin B into the Electrophilic Monomer Avrainvillamide in Cell Culture" J. Am. Chem. Soc. (2007), 129: pp. 4898-4899 (Year: 2007).*
Wulff, J., S. Herzon, R. Siegristand A. Myers, "Evidence for the Rapid Conversion of Stephacidin B into the Electrophilic Monomer Avrainvillamide in Cell Culture" J. Am. Chem. Soc. (2007), Supporting Information: p. S1-S25 (Year: 2007).*
Clark, "Halogens as oxidising agents", https://www.chemguide.co.uk/inorganic/group7/halogensasoas.html, last modified in May 2015. retrieved on May 13, 2020. (Year: 2015).*
Knölker, H. and C. Hofmann, "Transistion Metal Complexes in Organic Synthesis, Part 33. Molybdenum-mediated Total Synthesis of Girinimbine, Murrayacine, and Dihydroxygirinimbine", Tetrahedron Letters, vol. 37, No. 44, pp. 7947-7950, 1996. (Year: 1996).*
Gruner, K. and H. Knölker, "Palladium-catalyzed total synthesis of eucherestifoline using a one-pot Wacker oxidation and double aromatic C—H bond activation", Org. Biomol. Chem., 2008, 6, pp. 3902-3904. (Year: 2008).*
Arnim, et al., "Synthesis and phase behavior of new carbazole containing liquid crystal side chain polysiloxanes", Macro Chem. Physics, 197(9):2729-43 (1996).
Bard, et al., Caplus, "Electrochemical and photoelectrochemical studies of excess electrons im liquid ammonia", J Phys Chem., 84(10):1262-6 (1980) Abstract Only.
Beaulieu, et al., "An essential role for DNA methyltransferase DNMT3B in cancer cell survival", J Biol. Chem., 31:28176-81 (2002).
Brueckner, et al., "Epigenetic reactivation of tumor suppressor genes by a novel small-molecule inhibitor of human DNA methyltransferases", Cancer Res., 65:6305-6311 (2005).

(Continued)

*Primary Examiner* — Joseph R Kosack
*Assistant Examiner* — Sagar Patel
(74) *Attorney, Agent, or Firm* — Pabst Patent Group LLP

(57) ABSTRACT

Disclosed herein are methods of synthesizing mahanine and related compounds. The synthesis features an intramolecular aryl-alkyne isomerization, transition metal catalyzed cross-coupling and intramolecular carbazole forming reaction.

37 Claims, No Drawings

(56) References Cited

OTHER PUBLICATIONS

Chen, et al., "Increased cell growth and tumorigenicity in human prostate LNCaP cells by overexpression to cyclin D1", Oncogene., 16: 1913-1920 (1998).

Donninger, et al., "The RASSF1A tumor suppressor", J of Cell Sci., 120:3163-72 (2007).

Freeman, et al., "Triphenylphosphine-mediated reductive cyclization of 2-nitrobiphenyls: a practical and convenient synthesis of carbazoles" J. Org. Chem., 70:5014-19 (2005).

Goetz, Caplus, "Selective photobromination in the carbazole series", J Heterocyclic Chem., 11(3):445-7 (1974) Abstract Only.

Han, "Targeted prodrug design to optimize drug delivery", AAPS Pharmisci., 2(1):1-11 (2000).

Hudkins, et al., "Prodrug esters of the indolocarbazole cep-751 (kt-6587)", Bioorganic Med Chem Ltrs., 8:1873-6 (1998).

Illos, et al., "N-Danysyl-carbazoloquinone; a chemical and electrochemical fluorescent switch", Tetra Lttrs., 47:5543-6 (2006).

International Search Report PCT/US2009/004681 dated Dec. 10, 2009.

Isaacs, "Role of androgens in prostatic cancer", Vitam Horm., 49: 433-502 (1994).

Ito, et al., "New carbazole alkaloids from murraya euchrestifolia", Chem. Pharma. Bul., 39(7):1668-71 (1991).

Itoigawa, et al., "Antitumor agents 203 carbazole alkaloid murrayaquinone A and related synthetic carbazolequinones as cytotoxic agents", J Natl. Prod., 63(7):893-97 (2000).

Jagadeesh, et al., "Mahnine reverses an epifentically silenced tumor suppressor gene RASSFIA in human prostate cancer", Biochem. Biophy. Res. Comm., 362:212-17 (2007).

Kim, et al., "Co-operation and communication between the human maintenance and de novo DNA (cytosine-5) methyltransferases", EMBO J, 21:4183-95 (2002).

Kuzmin, et al., "The RASSF1A tumor suppressor gene is inactivated in prostate tumors and suppresses growth of prostate carcinoma cells", Cancer Res., 62: 3498-3502 (2002).

Li, et al., "DNA methylation in prostate cancer", Biochim. Biophys. Acta., 1704:87-102 (2004).

Liu, et al., "Frequent hypermethylation of the RASSF1A gene in prostate cancer", Oncogene., 21:6835-40 (2002).

Lyko, et al., "DNA methyltransferase inhibitors and the development of epigenetic cancer therapies", J Natl. Cancer Inst., 97:1498-1506 (2005).

Majumder, et al., "Role of de novo DNA methyltransferases and methyl CpG-binding proteins in gene silencing in a rat hepatoma", J of Biol. Chem., 277:16048-58 (2002).

Martinez-Palau, et al., "Synthesis of luminescent N-arylcarbazoles by cooper bronze-mediated reaction", Lett Org. Chem, 1:231-37 (2004).

Melisi, et al., "Recent developments in prodrug design; Drug targeting, pharmacological and pharmacokinetic improvements related to a reduction of adverse effects", Curr Topics Med Chem., 11(18):1 (2011).

Musgrove, et al., "Cyclin D1 induction in breast cancer cells shortens G1 and is sufficient for cells arrested in G1 to complete the cell cycle", PNAS, 91:8022-26 (1994).

Nakahara, et al., "Antimutagenicity of Some edible thai plants and a bioactive carbazole alkaloid, rnahanine, isolated from micromelum minutum", J Agric. Food Chem., 50:4796-4802 2002).

Pandeya, An introduction to Drug Design, p. 40, New Age Intl. Ltd Publishers, Delhi India, (1997).

Pfeifer, et al., "Methylation of the RASSF1A gene in human cancers", Biol Chem., 383:907-14 (2002).

Rautio, "Prodrug strategies in drug delivery", Prodrugs and Targeted Delivery: Towards Better ADME Properties, pp. 1-4, vol. 47 Wiley-Vch (2011).

Rong, et al., "Tumor suppressor RASSF1A is a microtubule-binding protein that stabilizes microtubules and induces G2/M arrest", Oncogene, 23: 8216-8230 (2004).

Roy, et al., "Mahanine, a carbozole alkaloid from micromelum minuturn, inhibits cell growth and induces apoptosis in U937 cells through a mitochondrial dependent pathway", Bri J Pharamacology, 145:145-155 (2005).

Roy, et al., "Mechanism of mahanine-induced apoptosis in human leukemia cells (HL-60)", Biochem. Pharmacol., 67:41-51 (2004).

Shivakumar, et al., "The RASSF1A tumor suppressor blocks cell cycle progression and inhibits cyclin D1 accumulation", Mol. Cell. Biol., 22:4309-18 (2002).

Sinha, et al., "Mahanine inhibits growth and induces apoptosis in prostate cancer cells through the deactivation of Akt and activation of caspases", The Prostate., 66:1257-65 (2006).

Song, et al., "The tumour suppressor RASSFIA regulates mitosis by inhibiting the APC-Cdc20 Complex", Nat. Cell Bio., 6(2):129-137 (2004).

Tombal, "Hormone therapy for prostate cancer: What have we done with Charles Huggins\ legacy", Eu. Urology, 61:26-28 (2012).

Ushiki, et al., "Fluorescence as a means for kinetic studies III bimolecular reaction of fluorescent reagent as quenching probes", Bull Chem. Soc. Jpn., 56:3181-2 (1983).

van der Weyden, et al., "The Ras-association domain family (RASSF) members and their role in human tumourigenesis", Biochem. Biophys. Ada., 1776:58-85 (2007).

Vos, et al., "A role for the RASSFIA tumor suppressor in the regulation of tubulin polymerization and genomic stability", Cancer Res., 64:4244-50 (2004).

Wang, et al., "Palladium-catalyzed homocoupling and cross-coupling reactions of aryl halides in poly(ethylene glycol", J. Org. Chem., 71:1284-87 (2006).

\* cited by examiner

SYNTHESIS OF MAHANINE AND RELATED COMPOUNDS

CROSS-REFERENCE TO RELATED APPLICATIONS

This application claims benefit of U.S. Provisional Application No. 62/182,706, filed Jun. 22, 2015. Application No. 62/182,706, filed Jun. 22, 2015, is hereby incorporated herein by reference in its entirety.

FIELD OF THE INVENTION

The invention is generally directed to the chemical synthesis of carbazole compounds, including mahanine and derivatives thereof.

BACKGROUND OF THE INVENTION

Mahanine is a carbazole-containing compound having the following structure:

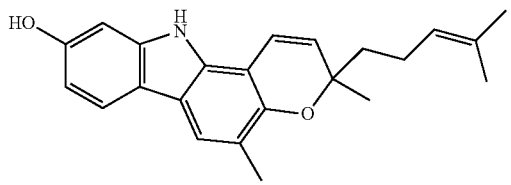 [SMILES: CC(C)=CCCC1(C)C=Cc2c(c(C)cc3c2[nH]c2cc(O)ccc23)O1]

It has been demonstrated that mahanine inhibits growth and induces apoptosis in both androgen-responsive, LNCaP and androgen-independent, PC3 prostate cancer cells in vitro. In addition, mahanine induces the expression of RASSF1A in human prostate cancer cells in a dose-dependent manner. The expression of RASSF1A is associated with a decrease in cyclin D1 message and protein levels and G0/G1 cell cycle arrest in prostate cancer cells. RASSF1A represses cyclin D1 transcription by inhibiting its promoter activity and addition of RASSF1A siRNA prevents this inhibition. Mahanine treatment also represses cyclin D1 transcriptional activity in prostate cancer cells. Mahanine induces the expression of an epigenetically silenced gene, RASSF1A, in prostate cancer cells. Expression of RASSF1A, in turn, is responsible for the repression/downregulation of cyclin D1 expression and eventually the cell cycle arrest at the G0/G1 phase.

Given its promising biological activity, a reliable source of large amounts of mahanine would be useful. Mahanine itself can be obtained from natural sources, including the leaf of the Indian curry tree *Murraya koeniigi*. However, such extractive protocols are limited to mahanine and a handful of other naturally occurring compounds. It would also be useful to access a wide variety of compounds structurally related to mahanine in order to further elucidate the biological processes described above, as well as to obtain compounds with different pharmacokinetic properties. Chemical synthesis represents the most straightforward method for obtaining non-naturally occurring analogs of mahanine, and may also represent a more practical route to the naturally occurring compound as well. At least one chemical synthesis of mahanine is known, however, this process does not reliably produce gram-scale and larger quantities of the compound.

It is an object of the invention to provide a synthetic route to mahanine capable of reliably producing gram scale (and larger) quantities of the compound.

It is a further object of the invention to provide a synthetic route which can be employed for the preparation of a wide variety of mahanine analogs.

SUMMARY OF THE INVENTION

Disclosed herein are methods for preparing mahanine and related carbazole compounds. The methods are compatible with a wide variety of functional groups, and thus a wide variety of mahanine analogs are obtainable from the disclosed methods.

DETAILED DESCRIPTION OF THE INVENTION

A. Definitions

The singular forms "a," "an," and "the" include plural reference unless the context clearly dictates otherwise. For example, reference to "a compound" includes a plurality of compounds and reference to "the compound" is a reference to one or more compounds and equivalents thereof known to those skilled in the art.

The term "can," "can be," and related terms is intended to convey that the subject matter involved is optional (that is, the subject matter is present in some embodiments and is not present in other embodiments), not a reference to a capability of the subject matter or to a probability, unless the context clearly indicates otherwise.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

As used herein, the term "analog" refers to a chemical compound with a structure similar to that of another (reference compound) but differing from it in respect to a particular component, functional group, atom, etc. As used herein, the term "derivative" refers to compounds which are formed from a parent compound by chemical reaction(s). These differences in suitable analogues and derivatives include, but are not limited to, replacement of one or more functional groups on the ring with one or more different functional groups or reacting one or more functional groups on the ring to introduce one or more substituents.

Numerical ranges disclosed in the present application of any type, disclose individually each possible number that such a range could reasonably encompass, as well as any sub-ranges and combinations of sub-ranges encompassed therein. A carbon range (i.e., $C_1$-$C_{10}$), is intended to disclose individually every possible carbon value and/or sub-range encompassed within. For example, a carbon length range of $C_1$-$C_{10}$ discloses $C_1$, $C_2$, $C_3$, $C_4$, $C_5$, $C_6$, $C_7$, $C_8$, $C_9$, and $C_{10}$, as well as discloses sub-ranges encompassed therein, such as $C_2$-$C_9$, $C_3$-$C_8$, $C_1$-$C_5$, etc.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30or fewer carbon atoms in its backbone (e.g., $C_1$-$C_{30}$for straight chain, $C_3$-$C_{30}$for branched chain), and more preferably 20or fewer. Likewise, preferred cycloalkyls have from 3-10carbon atoms in their ring structure, and more preferably have 5, 6 or 7carbons in the ring structure.

"Alkylaryl", as used herein, refers to an alkyl group substituted with an aryl group (e.g., an aromatic or heteroaromatic group). The terms "alkenyl" and "alkynyl" refer to unsaturated aliphatic groups analogous in length and possible substitution to the alkyls described above, but that contain at least one double or triple bond respectively.

"Aryl", as used herein, refers to 5-, 6- and 7-membered aromatic, heterocyclic, fused aromatic, fused heterocyclic, biaromatic, or biheterocyclic ring system, optionally substituted by halogens, alkyl-, alkenyl-, and alkynyl-groups. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (the rings are "fused rings") where at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heterocycle" or "heterocyclic", as used herein, refers to a cyclic radical attached via a ring carbon or nitrogen of a monocyclic or bicyclic ring containing 3-10ring atoms, and preferably from 5-6ring atoms, consisting of carbon and one to four heteroatoms each selected from the group consisting of non-peroxide oxygen, sulfur, and N(Y) where Y is absent or is H, O, ($C_{1-4}$)alkyl, phenyl or benzyl, and optionally containing 1-3double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4heteroatoms each selected from the group consisting of non-peroxide oxygen, sulfur, and N(Y) where Y is absent or is H, O, ($C_1$-$C_8$)alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

The terms ortho, meta and para apply to 1,2-, 1,3- and 1,4-disubstituted benzenes, respectively. For example, the names 1,2-dimethylbenzene and ortho-dimethylbenzene are synonymous.

As used herein, "heteroatom" refers to any atom other than hydrogen or carbon.

As used herein, "alkoxy" refers to a linear or branched carbon chain where at least one of the carbon-carbon bonds is interrupted by an oxygen atom.

As used herein, "alkylamine" refers to a linear or branched carbon chain where at least one of the carbon-carbon bonds is interrupted by a nitrogen atom of the formula NR, where R is defined below.

"Halogen", as used herein, refers to fluorine, chlorine, bromine, or iodine.

"Substituted", as used herein, means that the functional group contains one or more substituents attached thereon including, but not limited to, hydrogen, halogen, cyano, alkoxyl, alkyl, alkenyl, cycloalkyl, cycloalkenyl, aryl, heterocycloalkyl, heteroaryl, amine, hydroxyl, oxo, formyl, acyl, carboxylic acid (—COOH), —C(O)R', —C(O)OR', carboxylate (—COO—), primary amide (e.g., —CONH$_2$), secondary amide (e.g., —CONHR'), —C(O)NR'R", —NR'R", —NR'S(O)$_2$R", —NR'C(O)R", —S(O)$_2$R", —SR', and —S(O)$_2$NR'R", sulfinyl group (e.g., —SOR'), and sulfonyl group (e.g., —SOOR'); where R' and R" may each independently be hydrogen, alkyl, alkenyl, alkynyl, cycloalkyl, aryl, heterocycloalkyl and heteroaryl; where each of R' and R" is optionally independently substituted with one or more substituents selected from the group consisting of halogen, hydroxyl, oxo, cyano, nitro, amino, alkylamino, dialkylamino, alkyl optionally substituted with one or more halogen or alkoxy or aryloxy, aryl optionally substituted with one or more halogen or alkoxy or alkyl or trihaloalkyl, heterocycloalkyl optionally substituted with aryl or heteroaryl or oxo or alkyl optionally substituted with hydroxyl, cycloalkyl optionally substituted with hydroxyl, heteroaryl optionally substituted with one or more halogen or alkoxy or alkyl or trihaloalkyl, haloalkyl, hydroxyalkyl, carboxy, alkoxy, aryloxy, alkoxycarbonyl, aminocarbonyl, alkylaminocarbonyl and dialkylaminocarbonyl, or combinations thereof. In some instances, "substituted" also refers to one or more substitutions of one or more of the carbon atoms in a carbon chain (i.e., alkyl, alkenyl, cycloalkyl, cycloalkenyl, and aryl groups) which can be substituted by a heteroatom, such as, but not limited to, a nitrogen or oxygen.

As used herein, the term "leaving group," refers to a chemical fragment which can be displaced by a nucleophile. Exemplary leaving groups include halides such as chlorine, bromine, and iodine; sulfonyloxy ethers like mesylate, tosylate, and triflate; carboxylates such as trifluoromethyl acetate; and ionized heteroatoms such as —O$^+$R$_2$, —S$^+$R$_2$, and —N$^+$R$_3$.

As used herein, the term "protecting group," refers to a chemical fragment which can be used to deactivate a reactive functional group. The protecting group forms a covalent bond with the reactive functional group. The protecting group is removed under specific condition to regenerate the reactive functional group. Exemplary oxygen protecting groups include silyl ethers such as trimethylsilyl, tertbutyldimethylsilyl, triisopropylsilyl, and tertbutyldiphenylsilyl; esters such as acetate and benzoate; and ethers such as benzyl, methoxybenzyl, tetrahydropyranyl, triphenylmethyl, and methoxymethyl. Exemplary nitrogen protecting groups include carbamates such as tert-butoxycarbonyl, benzyloxycarbonyl, and 9-fluorenylmethyloxycarbonyl; amides such as acetamide, benzamide, trifluoroacetamide, and trichloroacetamide; phthalimides; amines such as benzyl and methoxybenzyl; and sulfonamides such as 4-methylphenylsulfonamide and nitrophenylsulfonamides.

"Pharmaceutically acceptable salt", as used herein, refer to derivatives of the compounds described herein where the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

"Purification," as used herein refers to the isolation, either completely or partially, of one or more selected reaction products. Complete isolation methods can include distillation and chromatographic purification, whereas examples of partial isolation include solvent washing and solvent exchange. Purification methods are known to those of skill in the art.

B. Methods of Making Carbazole Compounds

Carbazoles having the structure of Formula (1) can be prepared according to the methods disclosed herein. For example, the disclosed methods can be used to prepare carbazoles having the structure of Formula (1):

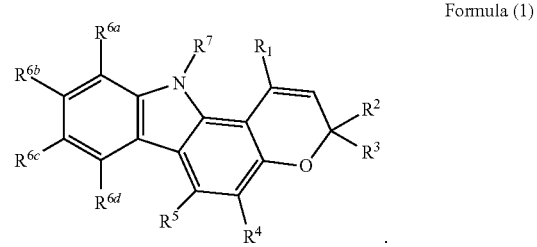

Formula (1)

In some embodiments, $R^1$-$R^{6a-6d}$ can independently represent:
(1) hydrogen,
(2) $C_1$-$C_{12}$alkyl,
(3) $C_2$-$C_{12}$alkenyl,
(4) $C_2$-$C_{12}$alkynyl,
(5) $C_6$-$C_{18}$aryl,
(6) $C_3$-$C_{12}$cycloalkyl,
(7) $C_1$-$C_{12}$heterocyclyl, (8) $C_1$-$C_{18}$heteroaryl,
(9) $C_1$-$C_{12}$alkoxy,
(10) $C_1$-$C_{12}$alkylamine
(11) $N(R)_2$,
(12) $NRC(=O)R$,
(13) $C(=O)N(R)_2$,
(14) $NRC(=O)OR$,
(15) $SR$,
(16) $SO_2R$,
(17) $S(=O)R$,
(18) $OH$,
(19) $OR$,
(20) $C(=O)R$,
(21) $COOH$,
(22) $C(=O)OR$,
(23) $OC(=O)R$,
(24) $OC(=O)OR$,
(25) $CN$,
(26) $N=C=O$,
(27) $P(=O)(R)_2$,
(28) $PO_3(R)_2$,
(29) halogen, or
(30) $NO_2$.

In some embodiments, $R^7$ can represent:
(1) hydrogen,
(2) $C_1$-$C_{12}$alkyl,
(3) $C_2$-$C_{12}$alkenyl,
(4) $C_2$-$C_{12}$alkynyl,
(5) $C_6$-$C_{18}$aryl,
(6) $C_3$-$C_{12}$cycloalkyl,
(7) $C_1$-$C_{12}$heterocyclyl,
(8) $C_1$-$C_{18}$heteroaryl,
(9) $C_1$-$C_{12}$alkoxy,
(10) $C_1$-$C_{12}$alkylamine,
(11) $C(=O)R$,
(12) $C(=O)OR$, or
(13) $C(=O)N(R)_2$.

In the formulae and compounds disclosed herein, each R (R lacking a superscript character) can be independently selected from hydrogen, $C_1$-$C_{12}$alkyl, $C_2$-$C_{12}$alkenyl, $C_2$-$C_{12}$alkynyl, $C_6$-$C_{18}$aryl, $C_3$-$C_{12}$cycloalkyl, $C_1$-$C_{12}$heterocyclyl, and $C_1$-$C_{18}$heteroaryl, $Si(R^{10})_3$. Each $R^{10}$ can be independently selected from $C_{1-12}$alkyl, $C_{6-12}$aryl, $C_1$-$C_{12}$alkoxy, and $C_1$-$C_{12}$alkylamine. In the case of $N(R)_2$, the two R groups can combine to form a cyclic ring.

In the formulae and compounds disclosed herein, each of the alkyl, alkenyl, alkynyl, aryl, cycloalkyl, heterocyclyl, heteroaryl, and alkoxy groups, of the carbon ranges specified above, can independently be substituted one or more times by:
(1) $C_1$-$C_{12}$alkyl,
(2) $C_2$-$C_{12}$alkenyl,
(3) $C_2$-$C_{12}$alkynyl,
(4) $C_6$-$C_{18}$aryl,
(5) $C_3$-$C_{12}$cycloalkyl,
(6) $C_1$-$C_{12}$heterocyclyl,
(7) $C_1$-$C_{18}$heteroaryl,
(8) $C_1$-$C_{12}$alkoxy,
(9) $C_1$-$C_{12}$alkylamine,
(10) $N(R)_2$,
(11) $NRC(=O)R$,
(12) $C(=O)N(R)_2$,
(13) $NRC(=O)OR$,
(14) $SR$,
(15) $SO_2R$,
(16) $S(=O)R$,
(17) $OH$,
(18) $OR$,
(19) $C(=O)R$,
(20) $COOH$,
(21) $C(=O)OR$,
(22) $OC(=O)R$,
(23) $OC(=O)OR$,
(24) $CN$,
(25) $N=C=O$,
(26) $P(=O)(R)_2$,
(27) $PO_3(R)_2$,
(28) halogen, or
(29) $NO_2$;
where R has the meanings defined above.

When a compound of Formula (1) contains an ionizable group, such as $COOH$, $SO_3H$, $PO_3H$, or $N(R)_2$, the compound of Formula (1) can also include salts, such as pharmaceutically acceptable salts, formed by combination with a suitable acid or base.

In some embodiments, $R^{6b}$ is hydroxyl and $R^1$, $R^5$, $R^{6a}$, $R^{6c}$, $R^{6d}$ and $R^7$ are hydrogen, $R^2$ and $R^4$ are alkyl, preferably methyl, and $R^3$ is an alkenyl group, preferably 4-methylpent-3-en-1-yl.

In some embodiments, the methods described herein produce a compound of Formula (1) which is the compound mahanine, (R)-3,5-dimethyl-3-(4-methylpent-3-en-1-yl)-3,11-dihydropyrano[3,2-a]carbazol-9-ol, having the following structure:

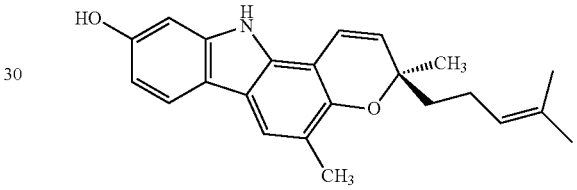

In some embodiments, compounds of Formula (1) when $R^7$ is hydrogen can be prepared from an azide-containing compound defined according to Formula (2):

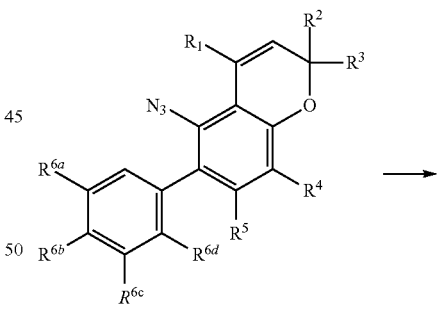

Formula (2)

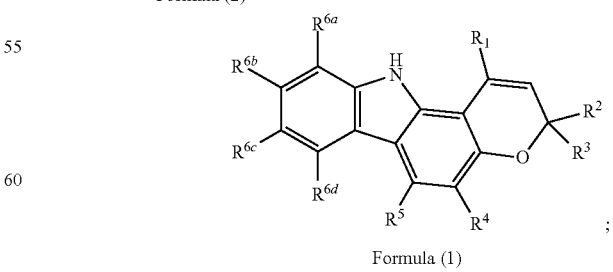

Formula (1)

$R_7 = H$ where $R^1$-$R^{6a-d}$ are as defined above.

The cyclization reaction forming compounds of Formula (1) can be carried out thermally, for instance by refluxing or otherwise heating in a high-boiling, inert solvent. Aromatic hydrocarbons are especially suitable solvents, and preferred solvents include, but are not limited to, benzene, toluene, ethyl benzene, chlorobenzene and one or more xylenes. In other embodiments, the reaction can be carried out in the presence of a C—N bond insertion catalyst which are known in the art. Rhodium dimers are suitable C—N insertion catalysts, and rhodium carboxylate dimers are especially preferred. Suitable rhodium catalysts include, but are not limited to, rhodium (II) perfluorobutyrate and rhodium (II) octanoate. Selection of suitable reaction conditions (i.e., time, temperature, pressure, choice of atmosphere (i.e., inert), reaction work up, purification, etc.) are within the skill of those in the art. In some embodiments, the reaction may not require any or any significant amount of purification.

When $R^7$ is hydrogen, the compound of Formula (1) can be converted to compounds in which $R^7$ is not hydrogen by reacting the compound of Formula (1) with a suitable base, capable of deprotonating the nitrogen with the $R^7$ hydrogen, and an electrophilic component, such as but not limited to, alkyl halides, such as methyl iodide. Such reactions are carried out in a suitable solvent and under suitable reaction conditions. Selection of suitable bases, electrophilic components, solvents, and reaction conditions (i.e., time, temperature, pressure, choice of atmosphere (i.e., inert), reaction work up, purification etc.) are known to those of skill in the art.

Compounds of Formula (2) can be prepared via a cross-coupling reaction of a compound according to Formula (3) with a compound according to Formula (4a):

in which $R^1$-$R^{6a\text{-}d}$ are as defined above, and $X^1$ and $X^2$ represent a pair of reactive moieties capable of undergoing a transition metal catalyzed cross coupling reaction. In some embodiments, one of $X^1$ or $X^2$ is halide, $SiF_3$, $Si(OEt)_3$, $N_2BF_4$, $NMe_3OTf$, $OCONR_2$, $OSO_2NR_2$, OTs, $OSO_2CH_3$, or $OSO_2CF_3$, and the other of $X^1$ or $X^2$ is a boron-containing functional group of the formula $B(R^8)_2$, where each $R^8$ can independently be hydroxy, alkyl, alkoxy or halide. When $R^8$ is alkyl or alkoxy, it is preferred that the two $R^8$ substituents and boron atom form a ring. Exemplary embodiments include, but are not limited to 9-borabicyclo[3.3.1]nonane and pinacol boronic esters. It is preferred that one of $X^1$ or $X^2$ is $B(OH)_2$ and the other is a halide, such as bromine. The cross-coupling reaction of the compounds of Formula (3) and (4a) can be carried out in the presence of a suitable catalyst and suitable ligand(s). In some embodiments, the catalyst is a Pd(0), Ni(0), Pd(II), or Ni(II) compound. Exemplary catalysts include, but are not limited to, $Pd(PPh_3)_4$, $Pd(OAc)_2$, $Pd_2(dba)_3$, $NiCl_2(dppf)$, and $NiCl_2(PCy_3)_2$. The reaction can be carried out in the presence of excess trialkyl phosphine compounds, or a mild base, or combinations thereof. Preferred trialkylphosphines include triphenylphosphines and tricyclohexylphosphines; preferred mild bases include metal carbonate salts, such as $K_2CO_3$ and $Na_2CO_3$. Such cross-coupling reactions are carried out in a suitable solvent and under suitable reaction conditions. Selection of suitable bases, ligands, solvents, and reaction conditions (i.e., time, temperature, pressure, choice of atmosphere (i.e., inert), reaction work up, purification etc.) are known to those of skill in the art.

In some other embodiments, the compound of Formula (2) can be prepared by reaction of a compound according to Formulae (3) and (4b) to give a compound of Formula (2-Z):

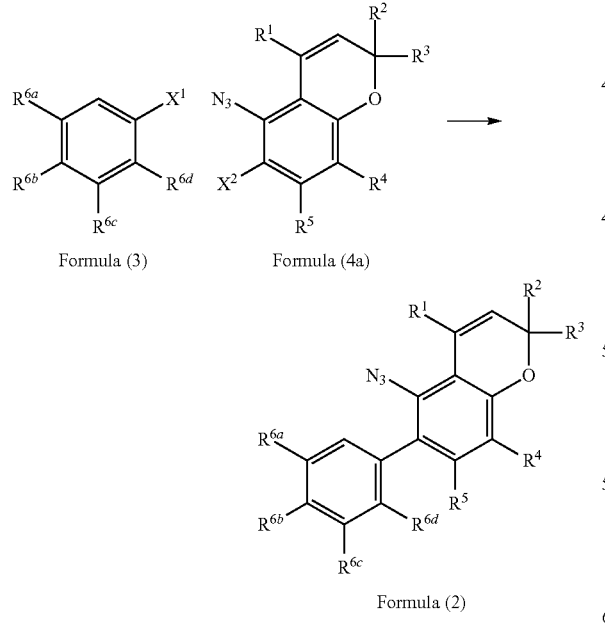

where $R^1$-$R^{6a\text{-}d}$, $X^1$ and $X^2$ are as defined above, and Z represents $NO_2$ or $N(R^9)_2$, where $R^9$ is either a suitable nitrogen protecting group or hydrogen, providing that at least one $R^9$ is not hydrogen. In some embodiments, the two $R^9$ groups can form a ring. The compounds of Formulae (3) and (4b) can be coupled using the same reagents and conditions for the transition metal catalyzed cross-coupling reaction of the compounds of Formulae (3) and (4a) described above.

The "Z" substituent is then converted into a free amine group ($NH_2$), followed by conversion into an azide ($N_3$) group. When Z is nitro, the free amine can be accessed by a reductive protocol/methods, which are known in the art.

Suitable reductive reagents include zinc/acetic acid, iron/acetic acid, sodium hydrosulfite, sulfide anions, tin chloride, samarium and catalytic hydrogenation using palladium, platinum, or Raney nickel catalyst. When Z is $N(R^9)_2$, the free amine can accessed by removal of the protecting group. The free amine can be converted to the azide using diazotization protocols/methods, which are known in the art, using $NaNO_2$ and $NaN_3$, or through oxidative processes, such as treatment with tert-butyl nitrite followed by an azide donor such as TMS-azide or sodium azide. Such diazotization reactions are carried out in a suitable solvent and under suitable reaction conditions. Selection of suitable solvents and reaction conditions (i.e., time, temperature, pressure, choice of atmosphere (i.e., inert), reaction work up, purification etc.) are known to those of skill in the art.

In certain embodiments, compounds of Formula (4b) can be converted to a compound of Formula (4a) using the reaction conditions described above for the conversion of the compound of Formula (2-Z) to Formula (2), namely a reaction which substitutes the Z substituent for an azide group.

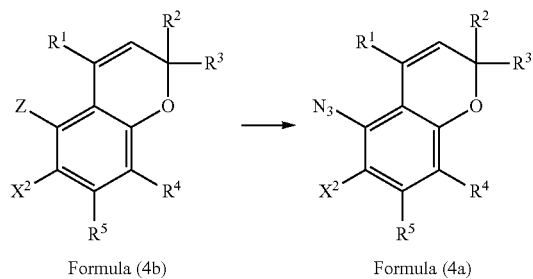

Formula (4b)          Formula (4a)

Compounds of Formula (4b) can be prepared by intramolecular cyclization of a compound according to Formula (5):

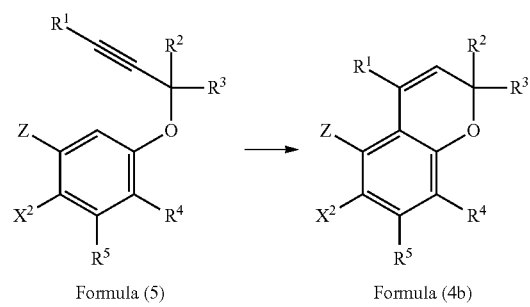

Formula (5)          Formula (4b)

where $R^1$-$R^5$, $X^2$, and Z are as defined above. In some embodiments, the cyclization reaction can be carried out thermally, for example, using microwave irradiation. In some other embodiments, the isomerization can be carried out by activating the alkyne to nucleophilic attack by the aromatic ring. Activation can be carried out with an electrophilic halogenating agent, including but not limited to, agents such as NIS, NBS, and $I_2$. In such embodiments, the vinyl-halide bond is reduced in a separate step to give the compound of Formula (4b). In some other embodiments, the isomerization can be carried out using a suitable Lewis acid catalyst. In some other preferred embodiments, the catalyst is a transition metal-based catalyst. Exemplary transition metal catalysts include salts of platinum, palladium, gold, and mercury. Such cyclization reactions are carried out in a suitable solvent and under suitable reaction conditions. Selection of suitable solvents and reaction conditions (i.e., time, temperature, pressure, choice of atmosphere (i.e., inert), reaction work up, purification etc.) are known to those of skill in the art.

Compounds of Formula (5) can be prepared by reacting a compound of Formula (6) with a compound of Formula (7):

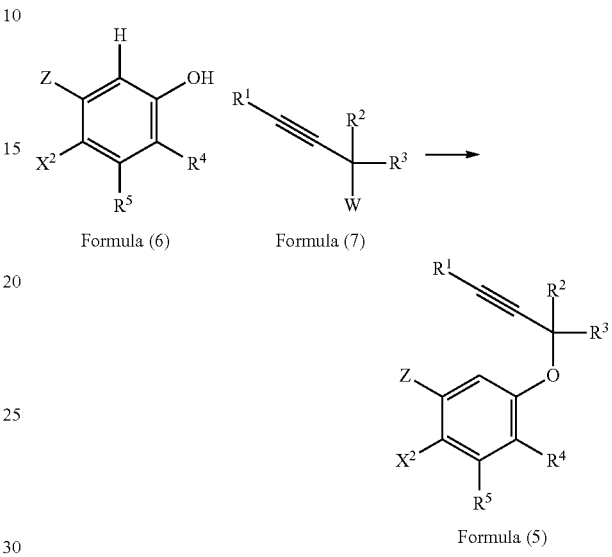

Formula (6)          Formula (7)

Formula (5)

where $R^1$-$R^5$, $X^2$, and Z are as defined above, and W represents a leaving group. In some embodiments, W is a leaving group such as, but not limited to, a chloride, bromine, iodine, mesylate, tosylate, besylate, triflouroacetate, methylcarbonate, or ethylcarbonate. The displacement reaction can be carried out in the presence of a metal salt, a base, or both. Exemplary metal salts include copper(II)chloride. The base can be a trialkylamine base such as triethylamine, diisopropylethyl amine, and 1,8-diazobicycloundec7-ene (DBU). Such reactions are carried out in a suitable solvent and under suitable reaction conditions. Selection of suitable solvents and reaction conditions (i.e., time, temperature, pressure, choice of atmosphere (i.e., inert), reaction work up, purification etc.) are known to those of skill in the art.

Compounds of Formula (7) can be prepared from a compound of Formula (8):

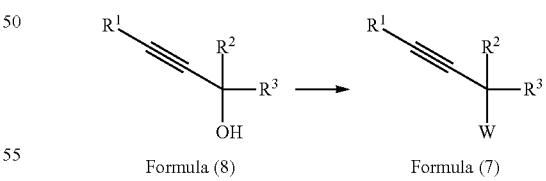

Formula (8)          Formula (7)

where $R^1$-$R^3$ are as defined above. Depending on the identity of $R^1$-$R^3$, the compound of Formula (8) can be obtained from commercial sources, or can be prepared using conventional chemical processes known in the art, such as reaction of a ketone or aldehyde with a nucleophilic terminal alkyne, or by nucleophilic addition or reduction of an acetylenic ketone.

Methods for converting a compound of Formula (8) to a compound of Formula (7) where the OH group is substituted for a W group, as defined above, are known in the art. Such methods include both in situ methods (i.e., one-pot methods) where the compound of Formula (7) is not isolated prior to combination with the compound of Formula (6). In some other embodiments, the compound of Formula (7) is isolated, either completely or partially, before reaction with the compound of Formula (6). Such substitution reactions are carried out in a suitable solvent and under suitable reaction conditions. Selection of suitable solvents and reaction conditions (i.e., time, temperature, pressure, choice of atmosphere (i.e., inert), reaction work up, purification etc.) are known to those of skill in the art.

The compounds according to the formulae described above may be subjected to purification to completely or partially isolate the desired reaction products/compounds. In the reactions described above, certain compounds represent intermediate compounds, where the final product is a compound according to Formula (1), and which may or may not require purification prior to their use in a subsequent reaction.

The compounds according to the formulae described above, whether subjected to any purification or not, may be characterized according to techniques known in the art, including but not limited to $^1$H and $^{13}$C NMR, and mass spectrometry.

The compounds according to the formulae described above may have one or more chiral centers and thus exist as one or more stereoisomers. Such stereoisomers can exist as a single enantiomer, a mixture of diastereomers or a racemic mixture are encompassed by the present disclosure. As used herein, the term "stereoisomers" refers to compounds made up of the same atoms having the same bond order but having different three-dimensional arrangements of atoms which are not interchangeable. The three-dimensional structures are called configurations. As used herein, the term "enantiomers" refers to two stereoisomers which are non-superimposable mirror images of one another. As used herein, the term "optical isomer" is equivalent to the term "enantiomer". As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached.

C. Methods of Obtaining Optically Enriched Material

Naturally occurring mahanine has the following absolute configuration:

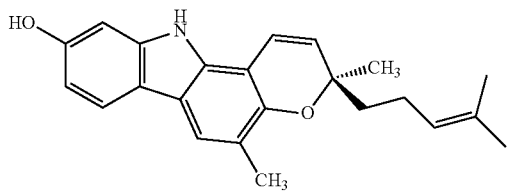 [SMILES: CC(C)=CCC[C@]1(C)C=Cc2c(c(C)cc3c2[nH]c2cc(O)ccc23)O1]

Although the compounds of Formulae 1-8 are depicted above without regard to stereochemistry, transformations involving either racemic or enantio-enriched substrates are within the scope of the disclosed processes.

Compounds of Formulae 1-8, having either the same absolute configuration as mahanine, or compounds having the opposite configuration, can be obtained using a number of different protocols, including chiral chromatography. In some embodiments, the compounds of Formulae 1-8 can be separated using a suitable chiral column material. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

In some other embodiments, diastereomeric mixtures of the two enantiomers can be prepared and separated. Exemplary methods include salt formation using an enantioenriched acid or base, followed by selective crystallization and esterification with enantio-enriched acids or alcohols.

EXAMPLES

A. Example 1

Total Synthesis of (±) Mahanine

Scheme 1 provides a scalable methodology for the process of synthesizing the natural product Mahanine. The eight step process will provide high purity mahanine in a scale needed for preclinical and clinical testing.

The synthesis of mahanine was enabled by a description of the synthetic methods including yields, analytical analysis and purity verification. All reagents and solvents were purchased from commercial suppliers and used as received unless noted otherwise. Flash column chromatography separations were done on a Biotage SP1 system monitoring at 254 and 310 nm. NMR spectra were recorded on a Varian 400 spectrometer at 25° C., operating at 400 MHz for $^1$H and 100 MHz for $^{13}$C NMR. The chemical shifts are expressed in ppm downfield from TMS as an internal standard. Reactions were monitored by thin-layer chromatography (TLC) on silica gel 60 glass slides. The structure of the synthesized compounds follows unequivocally from the mode of synthesis and the m/z values found in their low- and high-resolution mass spectra, TLC and NMR spectroscopy verified the purity.

4-bromo-2-methyl-5-nitrophenol (2)

KOH pellets (2.24 g, 40 mmol) was added to a solution of 4-bromo-2-methyl-5-nitrophenyl methyl carbonate (5.8 g, 20 mmol) in methanol (80 ml) at 50° C. with stirring, and the brick red solution was stirred at room temperature for 2 h then quenched with 1 N HCl to pH ~7. The mixture was concentrated and the residue was poured into a mixture of EtOAc-water (200 ml, v/v 3/1). After separation of the phases, the organic phase was washed with brine (30 ml) and dried over Na$_2$SO$_4$. After concentration and chromatography (hexane/EtOAc=3/1) 4-bromo-2-methyl-5-nitrophenol (4.1 g, 89%) was afforded as a yellow solid. $^1$H NMR (400M Hz, CDCl$_3$) δ: 7.47 (s, 1H), 7.38 (s, 1H), 5.40 (s, $^1$H), 2.29 (s, 3H); $^{13}$C NMR (100M Hz, CDCl$_3$) δ: 153.2, 136.6, 131.8, 112.3, 104.9, 15.7.

Scheme 1. Synthesis of Mahanine.

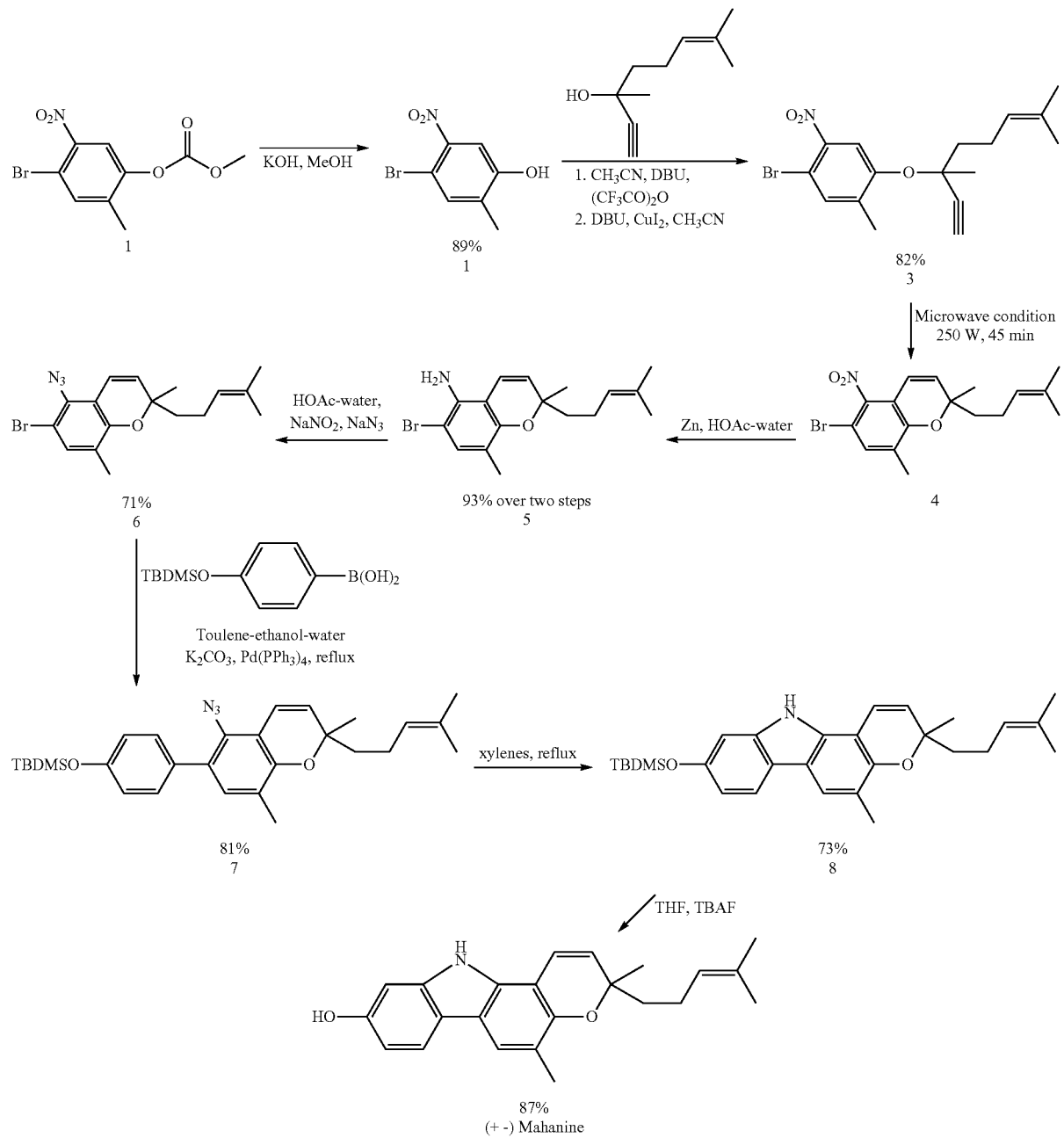

1-bromo-4-(3,7-dimethyloct-6-en-1-yn-3-yloxy)-5-methyl-2-nitrobenzene (3)

To a solution of 3,7-dimethyloct-6-en-1-yn-3-ol (1.52 g, 10 mmol) in anhydrous acetonitrile (10 mL) cooled to approximately −10-20° C. under $N_2$ atmosphere was added DBU (2.0 ml, 14 mmol). Trifluoroacetic anhydride (1.4 ml, 10 mmol) was added over a 25 min period while maintaining the temperature below −10° C. The resulting solution was allowed to stir at 0° C. for 45 min before the addition to the 4-bromo-2-methyl-5-nitrophenol solution as below described.

To a solution of 4-bromo-2-methyl-5-nitrophenol (2) (1.2 g, 5 mmol) in anhydrous acetonitrile (10 mL) cooled to approximately −10-20° C. under $N_2$ atmosphere was added DBU (1.2 ml, 7 mmol) and $CuCl_2$ (10 mg). The solution of the trifluoroacetate was maintained at 0° C., was added to the 4-bromo-2-methyl-5-nitrophenol solution over a 20 min period while maintaining the temperature below 0° C.

After being stirred for 5 h below 0° C., the mixture was poured into 30 ml saturated $NH_4Cl$ aq solution and the mixture was extracted with EtOAc (3×80 ml), dried with $Na_2SO_4$, then concentrated. After chromatography (hexane/acetone=95/5) gave the target compound 3 as yellow oil (1.5 g, 82%). (400M Hz, $CDCl_3$) δ: 8.10 (s, 1H), 7.47 (s, 1H), 5.15~5.11 (m, 1H), 2.71 (s, 1H), 2.32~2.23 (m, 5H), 1.99~1.92 (m, 2H), 1.69 (s, 3H), 1.65 (s, 3H), 1.62 (s, 3H); $^{13}$C NMR (100 M Hz, CDCl$_3$) δ: 153.2, 137.0, 136.0, 132.5, 122.9, 114.8, 106.0, 83.4, 76.7, 76.1, 42.5, 26.5, 25.6, 22.9, 17.5, 16.6.

6-bromo-2,8-dimethyl-2-(4-methylpent-3-enyl)-2H-chromen-5-amine (5)

A solution of compound 3 (3.0 g, 8.1 mmol) in DMF (10 ml) was treated with microwave at 250° C. for 45 min, the dark solution was cooled to room temperature and poured into 40 ml of water, which was extracted with EtOAc (3×80 ml). After combination of the organic phase, drying with Na$_2$SO$_4$, and concentration, the residue was used for next step without further purification.

A solution of the fresh prepared residue in HOAc-water (30 ml, v/v=2/1) was treated with Zn (5.2 g, 81 mmol) at 50° C. for 2 h. After filtration and concentration, the residue was dissolved in EtOAc (100 ml) and washed with saturated NaHCO$_3$ aq (30 ml), saturated brine (30 ml). After drying with Na$_2$SO$_4$ and concentration, the residue was chromatographed with 100%~10% hexane/EtOAc to afford the target compound 5 as a brown oil (2.5 g, 93% over two steps). $^1$H NMR (400 MHz, CDCl$_3$) δ: 7.05 (s, 1H), 6.46 (d, J=10.0 Hz, 1H), 5.59 (d, J=10.0 Hz, 1H), 5.15~5.11 (m, 1H), 2.06~2.03 (m, 5H), 1.69~1.65 (m, 5H), 1.56 (s, 3H), 1.36 (s, 3H); $^{13}$C NMR (100M Hz, CDCl$_3$) δ: 155.5, 150.7, 135.9, 132.8, 131.7, 129.2, 124.0, 118.6, 117.5, 109.6, 101.9, 77.4, 40.5, 25.6, 22.6, 17.5, 14.7.

5-azido-6-bromo-2,8-dimethyl-2-(4-methylpent-3-enyl)-2H-chromene (6)

NaNO$_2$ (414 mg, 6 mmol) was slowly added to a solution of compound 5 (1.4 g, 4.1 mmol) in HOAc-Water (30 ml, v/v=2/1) while cooling with ice water. After stirring for 30 min, NaN$_3$ (390 mg, 6 mmol) was slowly added over 20 minutes. The reaction was quenched 2 h later by adding sodium carbonate until the CO$_2$ evolution ceased. The mixture was extracted with EtOAc (3×80 ml). The organic phase was washed with saturated brine (30 ml), dried with Na$_2$SO$_4$ and concentrated. After chromatography in hexane, compound 6 was afforded as a yellow oil (1.0 g, 71%). $^1$H NMR (400 MHz, CDCl$_3$) δ: 7.12 (s, 1H), 6.66 (d, J=10.4 Hz, 1H), 5.64 (d, J=10.0 Hz, 1H), 5.10~5.07 (m, 1H), 2.11~2.04 (m, 5H), 1.69~1.66 (m, 5H), 1.56 (s, 3H), 1.36 (s, 3H); $^{13}$C NMR (100M Hz, CDCl$_3$) δ: 150.9, 133.7, 131.8, 130.9, 130.6, 125.2, 123.7, 118.1, 116.4, 107.6, 78.4, 40.9, 26.1, 25.6, 22.6, 17.5, 15.0.

(4-(5-azido-2,8-dimethyl-2-(4-methylpent-3-enyl)-2H-chromen-6-yl)phenoxy) (tert-butyl)dimethylsilane (7)

4-(tert-butyldimethylsilyloxy)phenylboronic acid (1.0 g, 4 mmol) was added to a mixture of compound 6 (1.0 g, 2.7 mmol), Na$_2$CO$_3$ (1.4 g, 13.5 mmol) and toluene-ethanol-water (60 ml, v/v/v=4/2/1), followed by tetrakis(triphenylphosphine) palladium(0) (240 mg, 0.2 mmol). After reflux under N$_2$ for 5 h, the mixture was cooled up to ambient temperature and concentrated to remove toluene and ethanol. The residue was diluted with EtOAc (100 mL) and washed with saturated brine (30 ml). After concentration and chromatography (hexane/EtOAc=99/1) compound 7 (1.1 g, 81%) was produced as a brown oil. $^1$J NMR (400 MHz, CDCl$_3$) δ: 7.18 (d, 8.4 Hz, 1H), J=7.05 (m, 1H), 6.66 (m, 3H), 6.48 (d, J=10.0 Hz, 1H), 5.40 (d, J=10.0 Hz, 1H), 4.90 (m, $^1$H), 1.94 (m, 5H), 1.49 (m, 5H), 1.37 (s, 3H), 1.19 (s, 3H), 0.78 (s, 9H), 0.00 (s, 6H); $^{13}$C NMR (100M Hz, CDCl$_3$) δ: 159.4, 159.1, 155.1, 136.7, 136.1, 135.5, 134.9, 134.2, 132.0, 128.4, 127.0, 124.6, 124.5, 122.9, 118.6, 82.5, 45.4, 30.6, 30.0, 27.1, 22.6, 21.9, 19.6, 0.0.

9-(tert-butyldimethylsilyloxy)-3,5-dimethyl-3-(4-methylpent-3-enyl)-3,11 dihydropyrano[3,2-a]carbazole (8)

Compound 7 (962 mg, 2 mmol) was refluxed in xylenes under N$_2$ overnight and the mixture was concentrated under reduced pressure to remove the solvent. After chromatography (hexane/acetone=5/1) compound 8 (670 mg, 73%) was produced as a brown oil. $^1$H NMR (400 MHz, methanol-d4) δ: 7.45 (d, J=8.4 Hz, 1H), 7.29 (s, 1H), 6.62 (m, 2H), 6.40 (m, 1H), 5.42 (d, J=10.0 Hz, 1H), 4.89 (m, 1H), 2.05 (s, 3H), 1.94 (m, 2H), 1.50 (m, 3H), 1.41 (s, 3H), 1.34 (s, 3H), 1.18 (s, 3H), 0.79 (s, 9H), 0.00 (s, 6H); $^{13}$C NMR (100M Hz, CDCl$_3$) δ: 153.4, 148.9, 140.5, 134.7, 131.6, 128.6, 124.2, 120.4, 119.6, 118.4, 118.1, 117.5, 116.7, 113.0, 104.2, 101.7, 77.9, 25.7, 15.6, 22.7, 18.2, 17.5, 16.0, 4.3.

(±) Mahanine

To a solution of 8 (300 mg, 0.6 mmol) in THF (5 ml) under N$_2$ and ice water cooling was added 3 ml of 1.0 M TBAF-THF. TLC (hexane/EtOAc=3/1) showed that the reaction was completely finished after 1 hour. EtOAc (30 ml) was added and the mixture was washed with sat. NaHCO$_3$ and dried with Na$_2$SO$_4$. After concentration and purification (hexane/EtOAc=7/1) (±) Mahanine was produced as gray solid (193 mg, 87%). HPLC analysis (charity column) showed product is a mixture of enantiomers; the ratio is approximately 1:1. $^1$H NMR (400 MHz, DMSO-d6) δ: 10.84 (brs, 1H), 9.20 (brs, $^1$H), 7.65 (d, J=8.4 Hz, 1H), 7.51 (s, 1H), 6.87 (d, J=9.6 Hz, 1H), 6.75 (s, 1H), 6.55 (d, J=8.4 Hz, 1H), 5.73 (d, =10.0 Hz, 1H), 5.09 (m, 1H), 2.21 (s, 3H), 2.08 (m, 2H), 1.69 (m, 2H), 1.60 (s, 3H), 1.52 (s, 3H), 1.38 (s, 3H); $^1$H NMR (400 MHz, methanol-d4) δ: 7.64 (d, J=8.4 Hz, 1H), 7.47 (s, 1H), 6.80 (d, J=6.8 Hz, 1H), 6.78 (s, 1H), 6.60 (dd, J=8.4 and 2.4 Hz, 1H), 5.64 (d, =10.0 Hz, 1H), 5.10 (m, 1H), 2.26 (s, 3H), 2.15 (m, 2H), 1.69 (m, 2H), 1.62 (s, 3H), 1.59 (s, 3H), 1.40 (s, 3H); $^{13}$C NMR (100M Hz, methanol-d4) δ: 154.7, 148.2, 141.6, 135.2, 130.8, 127.5, 124.0, 119.4, 119.0, 117.9, 116.8, 116.7, 116.4, 107.3, 104.1, 96.1, 77.5, 40.5, 24.8, 24.4, 22.4, 16.1, 14.8.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different leaving groups does not indicate that the listed leaving groups are obvious one to the other, nor is it an admission of equivalence or obviousness.

Every compound disclosed herein is intended to be and should be considered to be specifically disclosed herein. Further, every subgroup that can be identified within this disclosure is intended to be and should be considered to be specifically disclosed herein. As a result, it is specifically contemplated that any compound, or subgroup of compounds can be either specifically included for or excluded from use or included in or excluded from a list of compounds. For example, as one option, a group of compounds is contemplated where each compound is as described herein but where $R^7$ is not C(=O)R, C(=O)OR, or C(=O)N(R)$_2$.

Those skilled in the art will recognize, or be able to ascertain using no more than routine experimentation, many equivalents to the specific embodiments of the method and compositions described herein. Such equivalents are intended to be encompassed by the following claims.

We claim:

1. A method, wherein the method produces a compound of Formula (1):

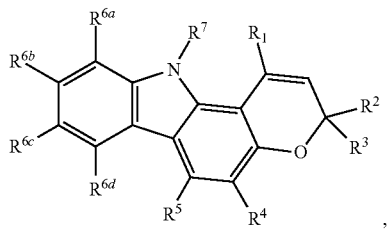

Formula (1)

wherein $R^1$-$R^{6a-6d}$ independently represent:
(1) hydrogen,
(2) $C_1$-$C_{12}$alkyl,
(3) $C_2$-$C_{12}$alkenyl,
(4) $C_2$-$C_{12}$alkynyl,
(5) $C_6$-$C_{18}$aryl,
(6) $C_3$-$C_{12}$cycloalkyl,
(7) $C_1$-$C_{12}$heterocyclyl,
(8) $C_1$-$C_{12}$heteroaryl,
(9) $C_1$-$C_{12}$alkoxy,
(10) $C_1$-$C_{12}$alkylamine,
(11) N(R)$_2$,
(12) NRC(=O)R,
(13) C(=O)N(R)$_2$,
(14) NRC(=O)OR,
(15) SR,
(16) SO$_2$R,
(17) S(=O)R,
(18) OH,
(19) OR,
(20) C(=O)R,
(21) COOH,
(22) C(=O)OR,
(23) OC(=O)R,
(24) OC(=O)OR,
(25) CN,
(26) N=C=O,
(27) P(=O)(R)$_2$,
(28) P$_3$(R)$_2$,
(29) halogen, or
(30) NO$_2$; and
$R^7$ represents:
(1) hydrogen,
(2) $C_1$-$C_{12}$alkyl,
(3) $C_2$-$C_{12}$alkenyl,
(4) $C_2$-$C_{12}$alkynyl,
(5) $C_6$-$C_{18}$aryl,
(6) $C_3$-$C_{12}$cycloalkyl,
(7) $C_1$-$C_{12}$heterocyclyl,
(8) $C_1$-$C_{18}$heteroaryl,
(9) $C_1$-$C_{12}$alkoxy,
(10) $C_1$-$C_{12}$alkylamine,
(11) C(=O)R,
(12) C(=O)OR, or
(13) C(=O)N(R)$_2$;
wherein each R is independently selected from the group consisting of hydrogen, $C_1$-$C_{12}$alkyl, $C_2$-$C_{12}$alkenyl, $C_2$-$C_{12}$alkynyl, $C_6$-$C_{18}$aryl, $C_3$-$C_{12}$cycloalkyl, $C_1$-$C_{12}$heterocyclyl, $C_1$-$C_{18}$heteroaryl, and Si(R$^{10}$)$_3$; wherein each $R^{10}$ is independently selected from the group consisting of $C_{1-12}$alkyl, $C_{6-12}$aryl, $C_{1-12}$alkoxy, and $C_{1-12}$alkylamine; and wherein the case of N(R)$_2$, the two R groups can combine to form a ring; and
wherein each of the alkyl, alkenyl, alkynyl, aryl, cycloalkyl, heterocyclyl, heteroaryl, and alkoxy groups listed above can independently be substituted one or more times by:
(1) $C_1$-$C_{12}$alkyl,
(2) $C_2$-$C_{12}$alkenyl,
(3) $C_2$-$C_{12}$alkynyl,
(4) $C_6$-$C_{18}$aryl,
(5) $C_3$-$C_{12}$cycloalkyl,
(6) $C_1$-$C_{12}$heterocyclyl,
(7) $C_1$-$C_{18}$heteroaryl,
(8) $C_1$-$C_{12}$alkoxy,
(9) $C_1$-$C_{12}$alkylamine,
(10) N(R)$_2$,
(11) NRC(=O)R,
(12) C(=O)NR$_2$,
(13) NRC(=O)OR,
(14) SR,
(15) SO$_2$R,
(16) S(=O)R,
(17) OH,
(18) OR,
(19) C(=O)R,
(20) COOH,
(21) C(=O)OR,
(22) OC(=O)R,
(23) OC(=O)OR,
(24) CN,
(25) N=C=O,
(26) P(=O)(R)$_2$,
(27) PO$_3$(R)$_2$,
(28) halogen, or
(29) NO$_2$;
wherein R has the meanings given above; or the compound of Formula (1) is a salt thereof;

wherein the method comprises at least one of the conversion steps (a), (b), and (c); and both conversion steps (d) and (e):

(a) conversion of a compound of Formula (2) to Formula (1)

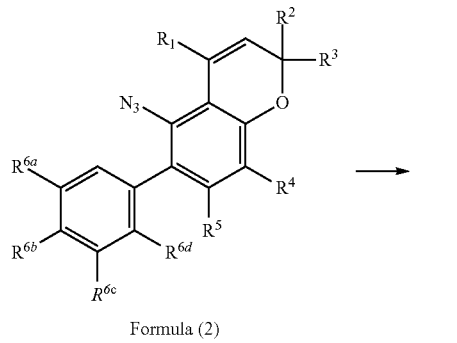

Formula (2)

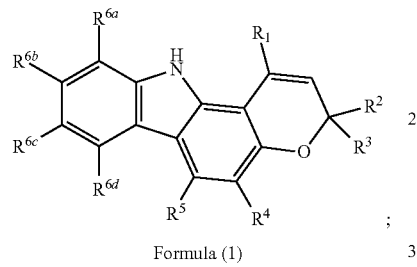

Formula (1)

$R_7 = H$ wherein $R^1$-$R^{6a-d}$ are as defined above and $R^7$ is a hydrogen;

(b) conversion of a compound of Formula (3) and Formula (4a) to a compound of Formula (2)

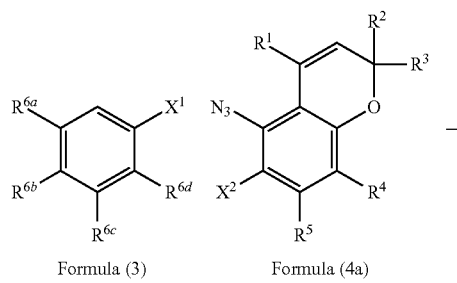

Formula (3)   Formula (4a)

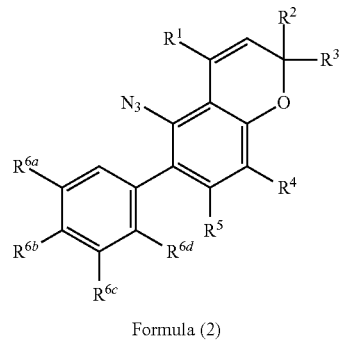

Formula (2)

wherein $R^1$-$R^{6a-d}$ are as defined above, one of $X^1$ or $X^2$ is halide, $SiF_3$, $Si(OEt)_3$, $N_2BF_4$, $NMe_3OTf$, $OCONR_2$, $OSO_2NR_2$, OTs, $OSO_2CH_3$ or $OSO_2CF_3$, and the other of $X^1$ or $X^2$ is a boron-containing functional group of the formula $B(R^8)_2$, wherein $R^8$ is hydroxy, alkyl, alkoxy or halide;

(c) conversion of a compound of Formula (3) and (4b) to a compound of Formula (2-Z)

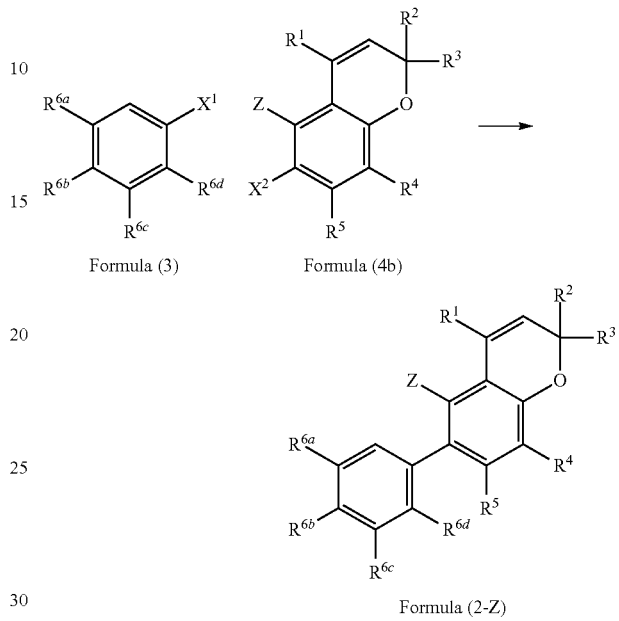

Formula (3)   Formula (4b)

Formula (2-Z)

wherein $R^1$-$R^{6a-d}$ and $X^2$ are as defined above, and Z is nitro or $N(R^9)_2$, wherein $R^9$ is either a nitrogen protecting group or hydrogen, providing that at least one $R^9$ is not hydrogen, and wherein the two $R^9$ groups can form a ring;

(d) conversion of a compound of Formula (5) to a compound of Formula (4b)

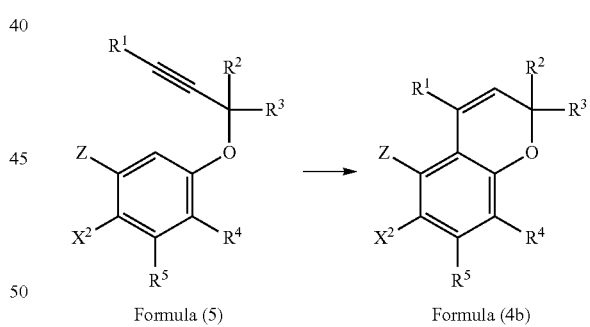

Formula (5)   Formula (4b)

wherein $R^1$-$R^{6a-d}$, Z, $X^1$ and $X^2$ are as defined above;

(e) conversion of a compound of Formula (6) and (7) to a compound of Formula (5)

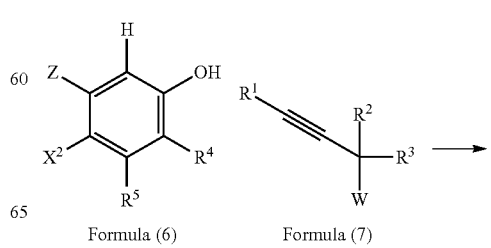

Formula (6)   Formula (7)

-continued

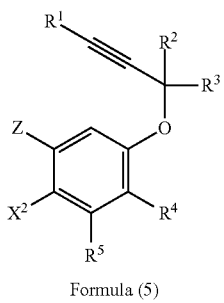

Formula (5)

wherein $R^1$-$R^{6a-d}$, Z and $X^2$ are as defined above, and W is a leaving group;
wherein the steps (a)-(e) are carried out in a solvent.

2. The method of claim 1, wherein the compound of Formula (1) wherein $r^{6b}$ is hydroxyl and $R^1$, $R^5$, $R^{6a}$, $R^{6c}$, $R^{6d}$, $R^7$ are hydrogen, $r^2$ and $r^4$ are alkyl, and $R^3$ is an alkenyl group.

3. The method of claim 2, wherein the compound of Formula (1) is (R)-3,5-dimethyl-3-(4-methylpent-3-en-1-yl)-3,11-dihydropyrano[3,2-a]carbazol-9-ol.

4. The method of claim 1, wherein step (a) the solvent is selected from the group consisting of benzene, toluene, ethyl benzene, chlorobenzene, and xylenes.

5. The method of claim 1, wherein step (a) comprises a catalyst.

6. The method of claim 5, wherein the catalyst is an insertion catalyst selected from the group consisting of rhodium (II) perfluorobutyrate and rhodium (II) octanoate.

7. The method of claim 1, wherein step (b) one of the $X^1$ or $X^2$ groups is selected from the group consisting of a halide, $SiF_3$, $Si(OEt)_3$, $N_2BF_4$, $NMe_3OTf$, $OCONR_2$, $OSO_2NR_2$, OTs, $OSO_2CH_3$, and $OSO_2CF_3$; and the other of $X^1$ or $X^2$ is a boron-containing functional group according to the formula $B(R^8)_2$, wherein each $R^8$ can independently be a hydroxy, alkyl, alkoxy or halide.

8. The method of claim 7, wherein one of $X^1$ or $X^2$ is $B(OH)_2$ and the other is a halide.

9. The method of claim 1, wherein step (b) comprises a catalyst and optionally one or more ligands.

10. The method of claim 9, wherein the catalyst is a Pd(0), Ni(0), Pd(II), or Ni(II) containing catalyst.

11. The method of claim 10, wherein the catalyst is selected from the group consisting of $Pd(PPh_3)_4$, $Pd(OAc)_2$, $Pd_2(dba)_3$, $NiCl_2(dppf)$, and $NiCl_2(PCy_3)_2$.

12. The method of claim 9, wherein step (b) comprises a base selected from carbonate salts.

13. The method of claim 1, wherein step (c) one of the $X^1$ or $X^2$ groups is selected from the group consisting of a halide, $SiF_3$, $Si(OEt)_3$, $N_2BF_4$, $NMe_3OTf$, $OCONR_2$, $OSO_2NR_2$, OTs, $OSO_2CH_3$, and $OSO_2CF_3$; and the other of $X^1$ or $X^2$ is a boron-containing functional group according to the formula $B(R^8)_2$, wherein each $R^8$ can independently be a hydroxy, alkyl, alkoxy, or halide.

14. The method of claim 13, wherein one of $X^1$ or $X^2$ is $B(OH)_2$ and the other is a halide.

15. The method of claim 1, wherein step (c) comprises a catalyst and optionally one or more ligands.

16. The method of claim 15, wherein the catalyst is a Pd(0), Ni(0), Pd(II), or Ni(II) containing catalyst.

17. The method of claim 15, wherein the catalyst is selected from the group consisting of $Pd(PPh_3)_4$, $Pd(OAc)_2$, $Pd_2(dba)_3$, $NiCl_2(dppf)$, and $NiCl_2(PCy_3)_2$.

18. The method of claim 15, wherein step (c) comprises a base selected from carbonate salts.

19. The method of claim 1, wherein step (d) further comprises an electrophilic halogenating agent selected from NIS, NBS, and $I_2$.

20. The method of claim 1, wherein step (d) further comprises a Lewis acid catalyst.

21. The method of claim 20, wherein the catalyst is a transition metal-based catalyst.

22. The method of claim 20, wherein the catalyst is a salt of platinum, palladium, gold, or mercury.

23. The method of claim 1, wherein step (e) comprises a metal salt, a base, or both.

24. The method of claim 23, wherein the metal salt is copper(II)chloride.

25. The method of claim 23, wherein the base is a trialkylamine base.

26. The method of claim 23, wherein the trialkylamine base is selected from the group consisting of triethylamine, diisopropylethyl amine, and 1,8-diazobicycloundec7-ene.

27. The method of claim 1, wherein in step (e) W is selected from the group consisting of a chloride, bromide, iodide, mesylate, tosylate, besylate, triflouroacetate, methylcarbonate, and ethylcarbonate.

28. The method of claim 2, wherein $R^2$ and $R^4$ are methyl.

29. The method of claim 2, wherein $R^3$ is 4-methyl-pent-3-ene-1-yl.

30. The method of claim 1, wherein when $R^1$, $R^2$, $R^3$, and $R^5$ are hydrogen, Z is $N(R^9)_2$, $X^2$ is a halide, and $R^4$ is C(=O)OR, then R is not an alkyl.

31. The method of claim 1, wherein $R^4$ independently represent:
(1) hydrogen,
(2) $C_1$-$C_{12}$alkyl,
(3) $C_2$-$C_{12}$alkenyl,
(4) $C_2$-$C_{12}$alkynyl,
(5) $C_6$-$C_{18}$aryl,
(6) $C_3$-$C_{12}$cycloalkyl,
(7) $C_1$-$C_{12}$heterocyclyl,
(8) $C_1$-$C_{12}$heteroaryl,
(9) $C_1$-$C_{12}$alkoxy,
(10) $C_1$-$C_{12}$alkylamine,
(11) $N(R)_2$,
(12) NRC(=O)R,
(13) C(=O)N(R)_2,
(14) NRC(=O)OR,
(15) SR,
(16) $SO_2R$,
(17) S(=O)R,
(18) OH,
(19) OR,
(20) C(=O)R,
(21) COOH,
(22) OC(=O)R,
(23) OC(=O)OR,
(24) CN,
(25) N=C=O,
(26) P(=O)(R)_2,
(27) $PO_3(R)_2$,
(28) halogen, or
(29) $NO_2$.

32. The method of claim 1, wherein the method comprises at least two of the conversion steps (a), (b), and (c).

33. The method of claim 1, wherein the method comprises four of the conversion steps (a), (b), (d), and (e).

34. The method of claim 1, wherein the method comprises four of the conversion steps (a), (c), (d), and (e).

35. The method of claim 1, wherein the method comprises the conversion steps (a), (b), (c), (d), and (e).

36. A method for the preparation of a compound of Formula (1):

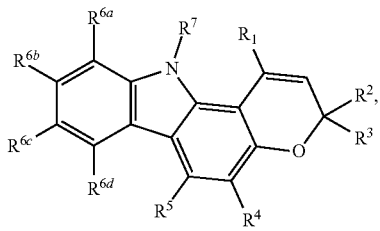

Formula (1)

wherein $r^1$-$R^{6a-6d}$ independently represent:
(1) hydrogen,
(2) $C_1$-$C_{12}$alkyl,
(3) $C_2$-$C_{12}$alkenyl,
(4) $C_2$-$C_{12}$alkynyl,
(5) $C_6$-$C_{18}$aryl,
(6) $C_3$-$C_{12}$cycloalkyl,
(7) $C_1$-$C_{12}$heterocyclyl,
(8) $C_1$-$C_{18}$heteroaryl,
(9) $C_1$-$C_{12}$alkoxy,
(10) $C_1$-$C_{12}$alkylamine,
(11) $N(R)_2$,
(12) $NRC(=O)R$,
(13) $C(=O)N(R)_2$,
(14) $NRC(=O)OR$,
(15) SR,
(16) $SO_2R$,
(17) $S(=O)R$,
(18) OH,
(19) OR,
(20) $C(=O)R$,
(21) COOH,
(22) $C(=O)OR$,
(23) $OC(=O)R$,
(24) $OC(=O)OR$,
(25) CN,
(26) $N=C=O$,
(27) $P(=O)(R)_2$,
(28) $PO_3(R)_2$,
(29) halogen, or
(30) $NO_2$; and $R^7$ represents:
(1) hydrogen,
(2) $C_1$-$C_{12}$alkyl,
(3) $C_2$-$C_{12}$alkenyl,
(4) $C_2$-$C_{12}$alkynyl,
(5) $C_6$-$C_{18}$aryl,
(6) $C_3$-$C_{12}$cycloalkyl,
(7) $C_1$-$C_{12}$heterocyclyl,
(8) $C_1$-$C_{18}$heteroaryl,
(9) $C_1$-$C_{12}$alkoxy,
(10) $C_1$-$C_{12}$ alkylamine,
(11) $C(=O)R$,
(12) $C(=O)OR$, or
(13) $C(=O)N(R)_2$;

wherein each R is independently selected from the group consisting of hydrogen, $C_1$-$C_{12}$ alkyl, $C_2$-$C_{12}$alkenyl, $C_2$-$C_{12}$alkynyl, $C_6$-$C_{18}$aryl, $C_3$-$C_{12}$cycloalkyl, $C_1$-$C_{12}$heterocyclyl, $C_1$-$C_{18}$heteroaryl, and $Si(R^{10})_3$;

wherein each $R^{10}$ is independently selected from the group consisting of $C_{1-12}$alkyl, $C_{6-12}$aryl, $C_{1-12}$alkoxy, and $C_{1-12}$alkylamine; and wherein the case of $N(R)_2$, the two R groups can combine to form a ring; and wherein each of the alkyl, alkenyl, alkynyl, aryl, cycloalkyl, heterocyclyl, heteroaryl, and alkoxy groups listed above can independently be substituted one or more times by:
(1) $C_1$-$C_{12}$alkyl,
(2) $C_2$-$C_{12}$alkenyl,
(3) $C_2$-$C_{12}$alkynyl,
(4) $C_6$-$C_{18}$aryl,
(5) $C_3$-$C_{12}$cycloalkyl,
(6) $C_1$-$C_{12}$heterocyclyl,
(7) $C_1$-$C_{18}$heteroaryl,
(8) $C_1$-$C_{12}$alkoxy,
(9) $C_1$-$C_{12}$alkylamine,
(10) $N(R)_2$,
(11) $NRC(=O)R$,
(12) $C(=O)NR_2$,
(13) $NRC(=O)OR$,
(14) SR,
(15) $SO_2R$,
(16) $S(=O)R$,
(17) OH,
(18) OR,
(19) $C(=O)R$,
(20) COOH,
(21) $C(=O)OR$,
(22) $OC(=O)R$,
(23) $OC(=O)OR$,
(24) CN,
(25) $N=C=O$,
(26) $P(=O)(R)_2$,
(27) $PO_3(R)_2$,
(28) halogen, or
(29) $NO_2$;

wherein R has the meanings given above; or the compound of Formula (1) is a salt thereof;

wherein the method comprises at least one of the following conversion steps (a), (b), and (c); and both conversion steps (d) and (e)

(a) conversion of a compound of Formula (2) to Formula (1)

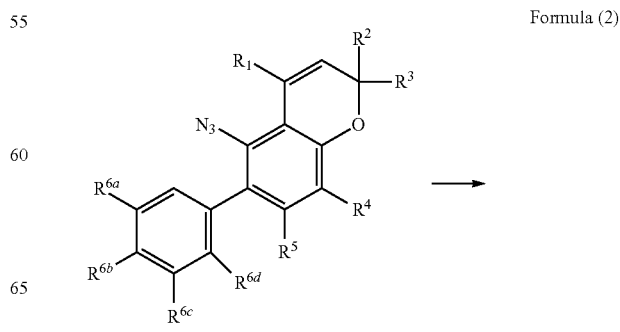

Formula (2)

27

-continued

Formula (1)

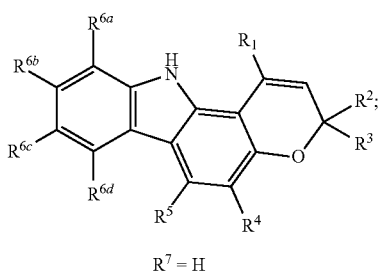

R⁷ = H wherein R¹-R⁶ᵃ⁻ᵈ are as defined above and R⁷ is a hydrogen;

(b) conversion of a compound of Formula (3) and Formula (4a) to a compound of Formula (2)

Formula (3)

Formula (4a)

Formula (2)

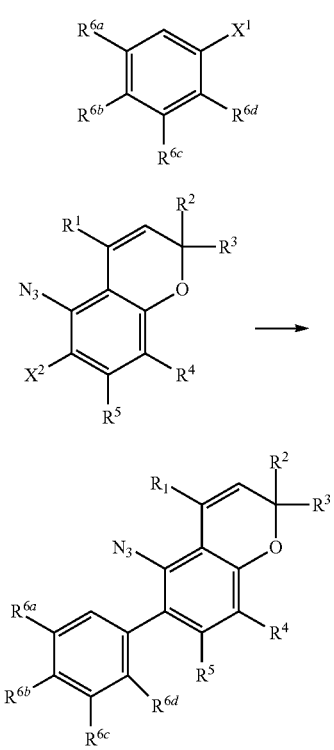

wherein R¹-R⁶ᵃ⁻ᵈ are as defined above, one of X¹ or X² is halide, SiF₃, Si(OEt)₃, N₂BF₄, NMe₃OTf, OCONR₂, OSO₂NR₂, OTs, OSO₂CH₃ or OSO₂CF₃, and the other of X¹ or X² is a boron-containing functional group of the formula B(R⁸)₂, wherein R⁸ is hydroxy, alkyl, alkoxy or halide;

(c) conversion of a compound of Formula (3) and (4b) to a compound of Formula (2-Z)

Formula (3)

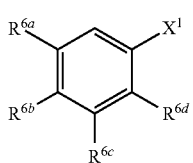

28

-continued

Formula (4b)

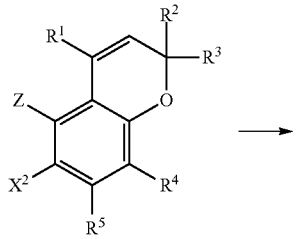

Formula (2-Z)

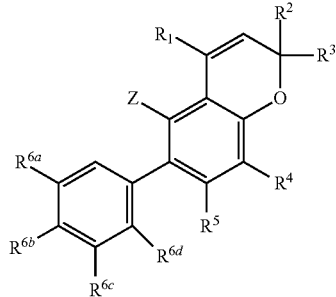

wherein R¹-R⁶ᵃ⁻ᵈ, X¹ and X² are as defined above, and Z is nitro or N(R⁹)₂, wherein R⁹ is either a nitrogen protecting group or hydrogen, providing that at least one R⁹ is not hydrogen, and wherein the two R⁹ groups can form a ring;

(d) conversion of a compound of Formula (5) to a compound of Formula (4b)

Formula (5)

Formula (4b)

wherein R¹-R⁶ᵃ⁻ᵈ, Z, X¹ and X² are as defined above;
wherein when R¹, R², R³, and R⁵ are hydrogen, Z is N(R⁹)₂, X² is a halide, and R⁴ is C(=O)OR, then R is independently selected from the group consisting of hydrogen, C₅-C₁₂alkyl, C₂-C₁₂alkenyl, C₂-C₁₂alkynyl, C₆-C₁₈aryl, C₃-C₁₂cycloalkyl, C₁-C₁₂heterocyclyl, C₁-C₁₈heteroaryl, and Si(R¹⁰)₃;
wherein when R¹, R⁴, and R⁵ are hydrogen, Z is nitro, X² is iodide, and R² is C₄alkenyl, then R³ is not methyl;
wherein when R¹, R⁴, and R⁵ are hydrogen, Z is nitro, X² is iodide, and R³ is C₄alkenyl, then R² is not methyl;
wherein R⁴ is not C(=O)OR;

(e) conversion of a compound of Formula (6) and (7) to a compound of Formula (5)

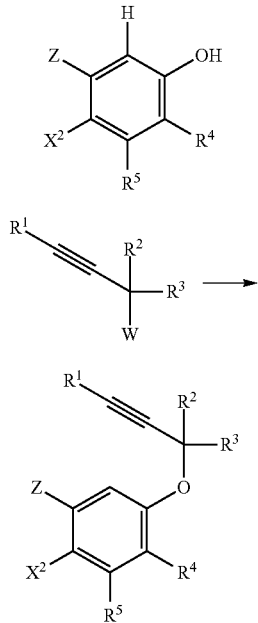

Formula (6)

Formula (7)

Formula (5)

wherein $R^1$-$R^{6a-d}$, Z and $X^2$ are as defined above, and W is a leaving group;

wherein when $R^1$, $R^4$, and $R^5$ are hydrogen, Z is nitro, $X^2$ is iodide, and $R^2$ is $C_4$alkenyl, then $R^3$ is not methyl;

wherein when $R^1$, $R^4$, and $R^5$ are hydrogen, Z is nitro, $X^2$ is iodide, and $R^3$ is $C_4$alkenyl, then $R^2$ is not methyl;

wherein the steps (a)-(e) are carried out in a solvent.

37. A method for the preparation of a compound of Formula (1):

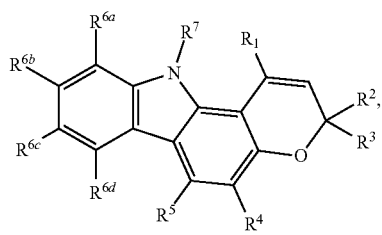

Formula (1)

wherein $R^1$-$R^{6a-6d}$ independently represent:
(1) hydrogen,
(2) $C_1$-$C_{12}$alkyl,
(3) $C_2$-$C_{12}$alkenyl,
(4) $C_2$-$C_{12}$alkynyl,
(5) $C_6$-$C_{18}$aryl,
(6) $C_3$-$C_{12}$cycloalkyl,
(7) $C_1$-$C_{12}$heterocyclyl,
(8) $C_1$-$C_{18}$heteroaryl,
(9) $C_1$-$C_{12}$alkoxy,
(10) $C_1$-$C_{12}$alkylamine,
(11) $N(R)_2$,
(12) $NRC(=O)R$,
(13) $C(=O)N(R)_2$,
(14) $NRC(=O)OR$,
(15) SR,
(16) $SO_2R$,
(17) $S(=O)R$,
(18) OH,
(19) OR,
(20) $C(=O)R$,
(21) COOH,
(22) $C(=O)OR$,
(23) $OC(=O)R$,
(24) $OC(=O)OR$,
(25) CN,
(26) N=C=O,
(27) $P(=O)(R)_2$,
(28) $PO_3(R)_2$,
(29) halogen, or
(30) $NO_2$; and
$R^7$ represents:
(1) hydrogen,
(2) $C_1$-$C_{12}$alkyl,
(3) $C_2$-$C_{12}$alkenyl,
(4) $C_2$-$C_{12}$alkynyl,
(5) $C_6$-$C_{18}$aryl,
(6) $C_3$-$C_{12}$cycloalkyl,
(7) $C_1$-$C_{12}$heterocyclyl,
(8) $C_1$-$C_{18}$heteroaryl,
(9) $C_1$-$C_{12}$alkoxy,
(10) $C_1$-$C_{12}$alkylamine,
(11) $C(=O)R$,
(12) $C(=O)OR$, or
(13) $C(=O)N(R)_2$;

wherein each R is independently selected from the group consisting of hydrogen, $C_1$-$C_{12}$alkyl, $C_2$-$C_{12}$alkenyl, $C_2$-$C_{12}$alkynyl, $C_6$-$C_{18}$aryl, $C_3$-$C_{12}$cycloalkyl, $C_1$-$C_{12}$heterocyclyl, $C_1$-$C_{18}$heteroaryl, and $Si(R^{10})_3$; wherein each $R^{10}$ is independently selected from the group consisting of $C_{1-12}$alkyl, $C_{6-12}$aryl, $C_1$-$C_{12}$alkoxy, and $C_1$-$C_{12}$alkylamine; and wherein the case of $N(R)_2$, the two R groups can combine to form a ring; and wherein each of the alkyl, alkenyl, alkynyl, aryl, cycloalkyl, heterocyclyl, heteroaryl, and alkoxy groups listed above can independently be substituted one or more times by:
(1) $C_1$-$C_{12}$alkyl,
(2) $C_2$-$C_{12}$alkenyl,
(3) $C_2$-$C_{12}$alkynyl,
(4) $C_6$-$C_{18}$aryl,
(5) $C_3$-$C_{12}$cycloalkyl,
(6) $C_1$-$C_{12}$heterocyclyl,
(7) $C_1$-$C_{18}$heteroaryl,
(8) $C_1$-$C_{12}$alkoxy,
(9) $C_1$-$C_{12}$alkylamine,
(10) $N(R)_2$,
(11) $NRC(=O)R$,
(12) $C(=O)NR_2$,
(13) $NRC(=O)OR$,
(14) SR,
(15) $SO_2R$,
(16) $S(=O)R$,
(17) OH,
(18) OR,
(19) $C(=O)R$,
(20) COOH,
(21) $C(=O)OR$,
(22) $OC(=O)R$,
(23) $OC(=O)OR$,
(24) CN,

(25) N=C=O,
(26) P(=O)(R)₂,
(27) PO₃(R)₂,
(28) halogen, or
(29) NO₂;

wherein R has the meanings given above; or the compound of Formula (1) is a salt thereof;

wherein the method comprises at least one of the following conversion steps (a), (b), and (c); and both conversion steps (d) and (e)

(a) conversion of a compound of Formula (2) to Formula (1)

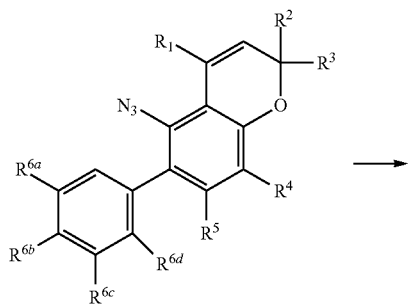

Formula (2)

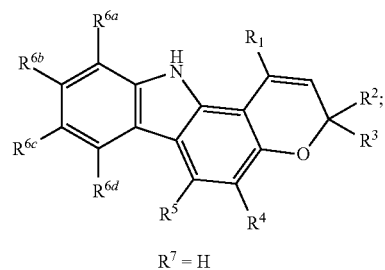

Formula (1)

wherein $R^1$-$R^{6a-d}$ are as defined above and $R^7$ is a hydrogen;

(b) conversion of a compound of Formula (3) and Formula (4a) to a compound of Formula (2)

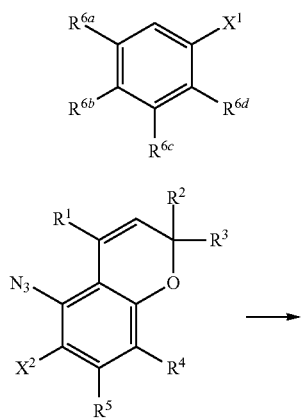

Formula (3)

Formula (4a)

Formula (2)

wherein $R^1$-$R^{6a-d}$ are as defined above, one of $X^1$ or $X^2$ is halide, SiF₃, Si(OEt)₃, N₂BF₄, NMe₃OTf, OCONR₂, OSO₂NR₂, OTs, OSO₂CH₃ or OSO₂CF₃, and the other of $X^1$ or $X^2$ is a boron-containing functional group of the formula B(R⁸)₂, wherein $R^8$ is hydroxy, alkyl, alkoxy or halide;

(c) conversion of a compound of Formula (3) and (4b) to a compound of Formula (2-Z)

Formula (3)

Formula (4b)

Formula (2-Z)

wherein $R^1$-$R^{6a-d}$ and $X^2$ are as defined above, and Z is nitro or N(R⁹)₂, wherein $R^9$ is either a nitrogen protecting group or hydrogen, providing that at least one $R^9$ is not hydrogen, and wherein the two $R^9$ groups can form a ring;

(d) conversion of a compound of Formula (5) to a compound of Formula (4b) in the presence of an electrophilic halogenating agent selected from NIS, NBS, and I₂

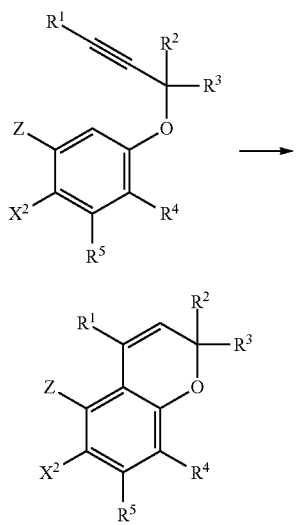

Formula (5)

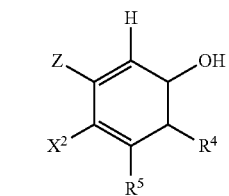

Formula (6)

Formula (4b)

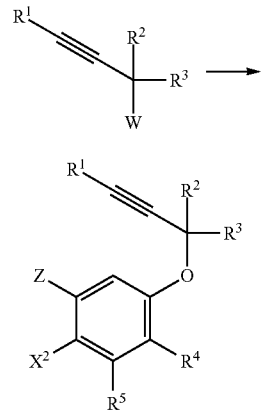

Formula (7)

Formula (5)

wherein $R^1$-$R^{6a-d}$, Z, $X^1$ and $X^2$ are as defined above;
wherein when $R^1$, $R^2$, $R^3$, and $R^5$ are hydrogen, Z is $N(R^9)_2$, $X^2$ is a halide, and $R^4$ is C(=O)OR, then R is independently selected from the group consisting of hydrogen, $C_5$-$C_{12}$alkyl, $C_2$-$C_{12}$alkenyl, $C_2$-$C_{12}$alkynyl, $C_6$-$C_{18}$aryl, $C_3$-$C_{12}$cycloalkyl, $C_1$-$C_{12}$heterocyclyl, $C_1$-$C_{18}$heteroaryl, and $Si(R^{10})_3$;
wherein when $R^1$, $R^4$, and $R^5$ are hydrogen, Z is nitro, $X^2$ is iodide, and $R^2$ is $C_4$alkenyl, then $R^3$ is not methyl;
wherein when $R^1$, $R^4$, and $R^5$ are hydrogen, Z is nitro, $X^2$ is iodide, and $R^3$ is $C_4$alkenyl, then $R^2$ is not methyl;
(e) conversion of a compound of Formula (6) and (7) to a compound of Formula (5)

wherein $R^1$-$R^{6a-d}$, Z and $X^2$ are as defined above, and W is a leaving group;
wherein when $R^1$, $R^4$, and $R^5$ are hydrogen, Z is nitro, $X^2$ is iodide, and $R^2$ is $C_4$alkenyl, then $R^3$ is not methyl;
wherein when $R^1$, $R^4$, and $R^5$ are hydrogen, Z is nitro, $X^2$ is iodide, and $R^3$ is $C_4$alkenyl, then $R^2$ is not methyl;
wherein the steps (a)-(e) are carried out in a solvent.

* * * * *